(12) United States Patent
Raith

(10) Patent No.: US 6,760,311 B1
(45) Date of Patent: Jul. 6, 2004

(54) THERMAL TRANSMISSION CONTROL OF WIRELESS DATA MODEM

(75) Inventor: Alex Krister Raith, Durham, NC (US)

(73) Assignee: Ericsson Inc., Research Triangle Park, NC (US)

( * ) Notice: Subject to any disclaimer, the term of this patent is extended or adjusted under 35 U.S.C. 154(b) by 0 days.

(21) Appl. No.: 09/196,127

(22) Filed: Nov. 20, 1998

(51) Int. Cl.⁷ .......................... G01R 31/08; H04Q 7/00; H04J 3/16
(52) U.S. Cl. ...................... 370/252; 370/328; 370/465; 455/433; 455/522
(58) Field of Search ................................ 370/231, 252, 370/321, 347, 392, 527, 529, 410, 465, 328; 708/141, 142; 455/115, 522, 507, 509, 517, 13.4, 435, 414, 419, 433, 226.2

(56) References Cited

U.S. PATENT DOCUMENTS

| | | | | |
|---|---|---|---|---|
| 4,843,351 A | * | 6/1989 | Edwards et al. .............. | 332/17 |
| 5,483,676 A | * | 1/1996 | Mahany et al. ............ | 455/67.4 |
| 5,519,886 A | | 5/1996 | Gilbert et al. | |
| 5,574,977 A | * | 11/1996 | Joseph et al. .............. | 455/58.1 |
| 5,590,133 A | | 12/1996 | Billstrom et al. ........... | 370/349 |
| 5,768,267 A | | 6/1998 | Raith et al. .................. | 370/329 |
| 5,848,062 A | * | 12/1998 | Ohno ......................... | 370/311 |
| 5,875,187 A | * | 2/1999 | Amin et al. ................. | 370/337 |
| 5,930,233 A | * | 7/1999 | Kanerva et al. ............ | 370/231 |
| 6,049,570 A | * | 4/2000 | Fukunaga et al. .......... | 375/240 |
| 6,128,505 A | * | 10/2000 | Sipila ......................... | 455/465 |
| 6,151,507 A | * | 11/2000 | Laiho et al. ................. | 455/466 |
| 6,266,685 B1 | * | 7/2001 | Danielson et al. .......... | 708/141 |
| 6,337,855 B1 | * | 1/2002 | Malkamaki ................. | 370/347 |

FOREIGN PATENT DOCUMENTS

| | | |
|---|---|---|
| CN | 1186575 | 7/1998 |
| EP | 0 800 282 | 10/1997 |
| EP | 0800282 A | 10/1997 |
| JP | 9-326749 | 12/1997 |
| JP | 09326749 | 12/1997 |
| WO | WO 9633555 | 10/1996 |
| WO | WO96/33555 | 10/1996 |
| WO | WO 98/10610 | 3/1998 |

\* cited by examiner

*Primary Examiner*—Duc Ho
(74) *Attorney, Agent, or Firm*—Coats & Bennett, P.L.L.C.

(57) ABSTRACT

A method for controlling temperature-related transmissions in radiocommunication systems. A mobile station includes a measuring device for determining operating temperature. When the measured temperature exceeds a predetermined threshold temperature, the mobile station can reduce its transmission rate, thereby reducing power dissipation within the device. The mobile station informs the system of the rate reduction, whereby the system can reallocate released resources, e.g., timeslots and/or spreading codes. The mobile station can also inform the user of the change in transmission rates and/or the temperature of the mobile station, whereupon the user can move to a better transmitting location. The mobile station can also take into account the transmit status of the current connection in determining when to reduce the transmission rate.

77 Claims, 6 Drawing Sheets

THERMAL TRANSMISSION CONTROL OF WIRELESS DATA MODEM

BACKGROUND

The present invention generally relates to the field of communications systems and, more particularly, to the field of radio communications systems wherein transmissions can occur at variable rates.

Commercial communication systems and, in particular, cellular radiotelephone systems have experienced explosive growth in the past decade. This growth is due, at least in part, to the improvement in the number and quality of services provided by radiocommunication systems. For example, early systems were designed primarily to support voice communications. However, cellular radiocommunication systems now provide many additional services including, for example, paging, messaging and data communications (e.g., to support Internet communication). Some of these new services make higher throughputs (i.e., than needed for voice communication) very desirable.

In order to provide these various communication services, a corresponding minimum user bit rate is required. For example, for voice and/or data services, user bit rate corresponds to voice quality and/or data throughput, with a higher user bit rate producing better voice quality and/or higher data throughput. The total user bit rate is determined by a selected combination of techniques, e.g., speech coding, channel coding, modulation scheme, and the air interface resources allocated to the connection, i.e., for a TDMA system, the number of assignable time slots, for a CDMA system the number of spreading codes.

Today's cellular phones transmit at a net data rate of about 10 kbit/s. In the future, it is expected that cellular modems will be able to receive and transmit several hundreds of kilobits per second. One example is the GSM-based packet data system referred to as General Packet Radio Service (GPRS). However, in order to provide these higher throughput rates while at the same time maintaining existing cell sizes (which latter criteria is strongly desired by network operators), the transmit power must increase correspondingly. Under this scenario, especially for small wireless modems, such as those which can be built-in to small handheld phones and for wireless modem cards inserted into PCs or laptops, an increase in average power will generate more heat than can be cooled off by these small devices.

For example, power amplifiers used in mobile phones and modems in the transmit path are not perfect, i.e., not all power is transformed into electromechanical waves. Depending on the modulation scheme and implementation, roughly half of the generated power is lost in the form of heat dissipation in the power amplifier. This heat can be damaging to the modem or annoying to the end user in the case of a handheld device. Thus, lack of heat dissipation rather than issues of complexity associated with higher bit rates may limit the maximum bit rate that a small phone can transmit.

For packet data operation the activity is often very bursty. This reduces the average power consumption. The burstyness of packet data transmissions is governed by the application, i.e., the instantaneous use. However, the mobile phone designer typically assumes the worst case scenario, i.e., that there will be times when the application will transmit for an extended period of time (related to the heat dissipation time constant) at its full bit rate capability. Thus, mobiles may be designed to restrict their transmitted bit rate such that the temperature of the devices is limited to a safe level even during worst case periods of usage.

Some documents describe attempts to combat increases in device temperature by monitoring the device temperature and adjusting the operation of the device based on the monitored temperature. For example, EP 800,282 describes a system wherein a temperature sensor monitors the temperature within a portion of the system. When the monitored temperature exceeds a threshold temperature, then the transmission rate associated with a speech codec is decreased. Similarly, the abstract of JP 9/326749 describes a system wherein data packets are transmitted in consecutive timeslots when a temperature of a power module is less than a threshold, but wherein packet data transmission is made intermittently when the power module becomes too hot.

Although these conventional solutions partially address the temperature/transmission rate problem described above; they do so in a unilateral manner, i.e, the mobile station makes a temperature determination and unilaterally adjusts transmissions accordingly. Applicant envisions additional features which provide a cooperative solution between the system, mobile unit and user for addressing temperature/transmission rate issues, whereby overall system operation and user knowledge is enhanced.

SUMMARY

According to exemplary embodiments of the present invention, a mobile station measures its operating temperature and compares that temperature with a threshold. When the measured temperature exceeds the threshold, the mobile station reduces its consumed transmit power by reducing its transmission rate. The mobile station may first request the reduction from the system, or may independently decide to reduce its transmission rate. In either case, the mobile station will transmit an indication of the reduced transmission rate to the system. In this way, the system can reallocate resources, e.g., by allocating released uplink timeslots to other mobile stations, by allocating released uplink spreading codes to other mobile stations and/or by allocating additional downlink timeslots to the mobile station that is reducing its transmission rate.

According to other exemplary embodiments of the present invention, the mobile station can inform the user of the reduction in transmission rate, as well as provide an indication that the reduction is due to increased temperature of the mobile station. The heat alert can take different forms, including a displayed icon, a warning sound or a voice alert. This enables the user to move to a better transmit position, which may result in the system instructing the mobile station to reduce its transmit power, thereby reducing the mobile station's temperature.

According to other exemplary embodiments of the present invention, reductions in transmission rate can be decided based both on the measured temperature and on the transmit status of the mobile station. For example, if the mobile station is in the middle of a higher layer message, it may continue to transmit lower layer frames even after the first temperature threshold is exceeded. However, continued transmission can be predicated on the measured temperature being lower than a second threshold. By permitting the mobile station to complete a higher layer message, retransmission and processing delay are minimized.

BRIEF DESCRIPTION OF THE DRAWINGS

Other features and advantages of the present invention will become apparent from the following detailed description, taken in conjunction with the accompanying drawings, which illustrate, by way of example, the principles of the invention.

DETAILED DESCRIPTION

According to exemplary embodiments of the present invention, the temperature of the mobile station is monitored and used in a number of different ways to adjust system and mobile station operation and to keep the user informed of the mobile station's performance so that he or she can also act accordingly. As evidenced by the aforedescribed EP 800,282 and the abstract of JP 9/326749, the physical implementation of temperature sensors and devices for reading the measured temperatures in wireless communication devices per se is known and, therefore, is not described in great detail herein. The disclosures of these documents are expressly incorporated here by reference. Instead methods of (and devices for) using this information, for example, to inform the system of operational changes, to reallocate resources within the system and to inform the user of the temperature-related operational change, according to the present invention are described more fully.

The following description is written in terms of a cellular radiotelephone system, but it will be understood that Applicant's invention is not limited to that environment. More specifically, the following description is written using terms which may be associated with TIA/EIA 136 and GSM/GPRS compliant systems, but it will be understood by those skilled in the art that the present invention may be implemented in other communication applications including those which are designed in accordance with other standards, e.g., IS-95 or PDC, as well as those which use other access methodologies, e.g., CDMA.

Figure 1:
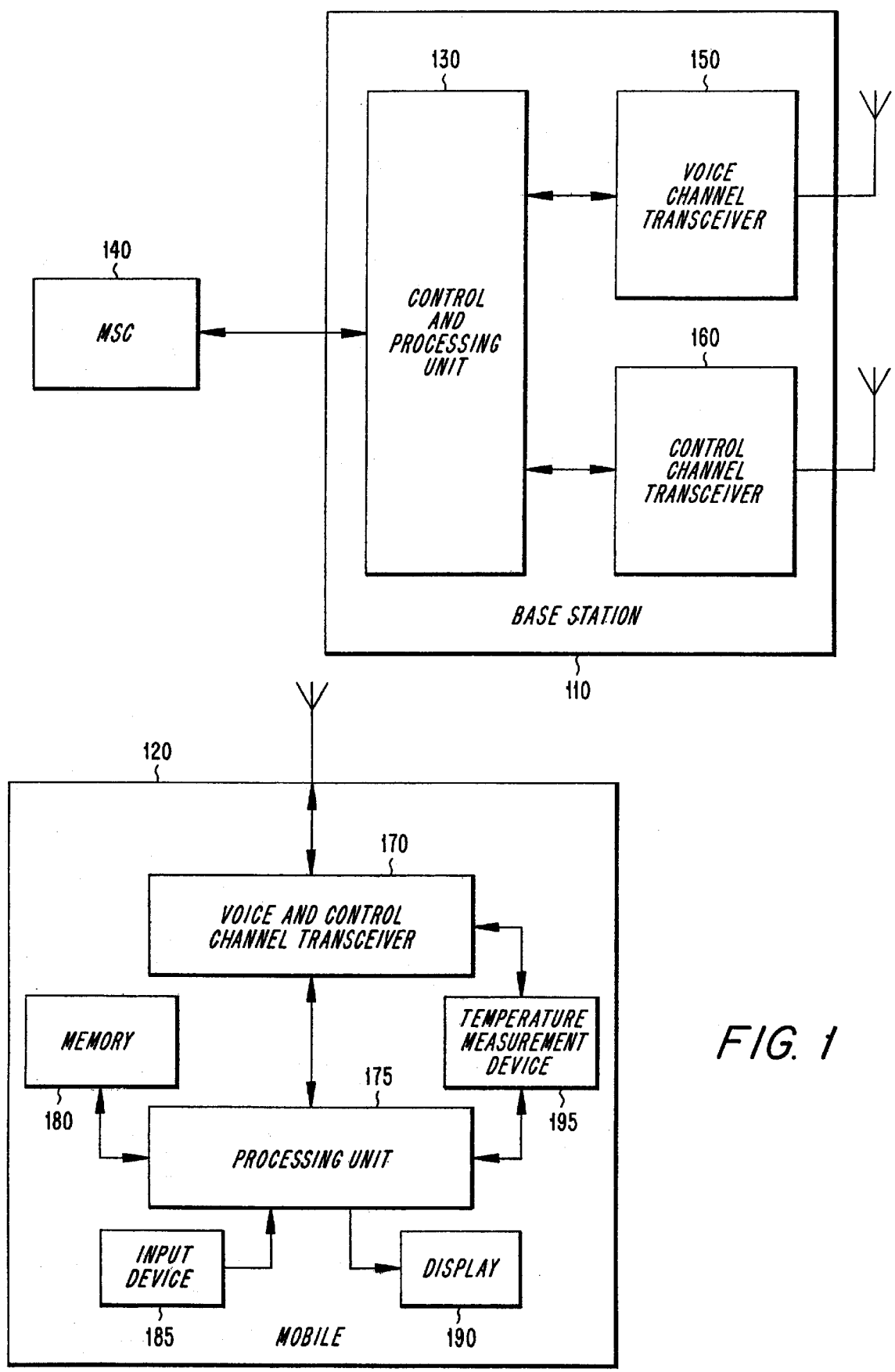
FIG. 1 is a block diagram of an exemplary cellular mobile radiotelephone system.

FIG. 1 represents a block diagram of an exemplary cellular mobile radiotelephone system, including an exemplary base station 110 and mobile station 120, in which the present invention can be implemented. The base station includes a control and processing unit 130 which is connected to the mobile service switching center, MSC 140, which in turn is connected to a packet switched network via a serving GPRS support node, SGSN (not shown). General aspects of packet data radiocommunication systems are known in the art, as described, for example, by U.S. Pat. No. 5,590,133 to Billstrom et al. and U.S. Pat. No. 5,768,267 to Raith et al., both of which are incorporated in this application by reference.

The base station 110 handles a plurality of voice channels through a voice channel transceiver 150, which is controlled by the control and processing unit 130. Also, each base station includes a control channel transceiver 160, which may be capable of handling more than one control channel. The control channel transceiver 160 is controlled by the control and processing unit 130. The control channel transceiver 160 broadcasts control information over the control channel of the base station or cell to mobiles locked to that control channel. It will be understood that the transceivers 150 and 160 can be implemented as a single device, like the voice and control transceiver 170 in mobile station 120.

Mobile station 120 receives the information broadcast on a control channel at its voice and control channel transceiver 170. Then, the processing unit 175 evaluates the received control channel information, which can include characteristics of cells that are candidates for the mobile station to lock on to, and determines on which cell the mobile should lock. In the present invention the broadcast control channel can also be used to send information to the mobile station indicating certain capabilities of the base station, e.g., those associated with throughput (bit rate). Thus, this base station capability information may include information regarding the base station's support (if any) for multi-slot operation, multi-code operation and/or different modulation/coding schemes, which characteristics, among others, impact transmission/reception throughput. Once the mobile station has received this information, it can compare its own capabilities with those supported by the base station and determine the maximal bit rate achievable in that cell.

The mobile station 120 also includes an input device 185, such as a numeric keypad, which allows a user to interact with the mobile station. A display device 190, such as an LCD screen, provides a visual display of information to the user, e.g., indicators of maximal and/or predicted throughput and/or temperature warnings as described below. A temperature measurement device or sensor 195 measures the heat within the mobile station's housing, e.g., proximate the power amplifier (not shown) and provides temperature information to the processor 175. In addition to being configured as a cellular telephone, the mobile station may also be a PC card, e.g., a card designed in accordance with the PCMCIA standard, which is connected to a personal computer, e.g., a laptop. In this latter case the display device would be the PC monitor.

The mobile station also includes memory 180, which may include a pre-programmed address having the terminal's capabilities and one or more temperature thresholds stored therein. Since the terminal's capabilities may be limited by the type of subscription held by the user, such limitations would need to be known by the terminal and/or the system for throughput calculation purposes. This information may be provided to the terminal in a number of ways. For example, the information may be stored on the user's subscriber interface module (SIM) card which is inserted in the terminal or, the subscription information may be signaled to the terminal at call setup/login.

At call set-up (or at the start of a transaction), the system determines the initial transmission rate at which the connection will operate. The system can identify the capability of the mobile station in various ways. For example, the system can retrieve the mobile station's capabilities from the home location register (HLR) using the mobile station's MIN and/or IMSI, the system can receive this information from the mobile station at registration, e.g., via a capability report or a class mark, the system can receive this information from the mobile station at call set-up (or at the start of a transaction), e.g., via a capability report or a class mark. Then the system can then assign transmission resources, e.g., timeslots and/or codes, based on the mobile station's capabilities, among other factors.

As will be appreciated by those skilled in the art, for the base station 110 to correctly detect the bits sent by mobile 120, the received power of the bits must be above the noise and interference level to a degree dependent on the particular access method. The signal-to-noise ratio (SNR) may be measured after any channel decoding and despreading employed. Since packet data systems typically incorporate techniques for retransmission of unrecoverable blocks of data (ARQ techniques), low SNR results in greater delay and lower throughput. More specifically, when the channel becomes poor, the mobile more frequently has to retransmit a block rather than sending a new block of data.

However, for a given quality of service (i.e, as characterized by throughput and delay), the higher the transmitted bit rate, the more total power is required in the mobile to maintain a given SNR, and thereby quality of service in the base station. Each bit requires a certain power to transmit. The power requirement in the transmitter is then proportional to the number of transmitted bits. This is independent of the access methodology, e.g., FDMA, TDMA, CDMA, OFDM or any combination of these basic concepts.

Of course, if the mobile 120 moves closer to the base station 110, the SNR in the base station 110 increases. Thus, an alternative to the rule that increased power is required for increased bit rate, is to effectively make the cell size dependent on the bit rate. However, network operators would generally prefer, within limitations based on cost, size and complexity, to offer a ubiquitous data service irrespective of the location of the user and to maintain current cell sizes.

An example will serve to better illustrate the relationship between throughput and temperature within the mobile station. In the GSM system there are eight time slots in the TDMA frame. For circuit switched operation, eight users can be multiplexed on a single carrier. For each full-rate traffic channel, a user is assigned one time slot per TDMA frame. A typical GSM mobile may transmit with 1 W. The average power consumption is then ⅛ W, since the mobile station is only active for ⅛ of the time. Since the TDMA frame is very short (a few milliseconds), the temperature will not vary much during a TDMA frame, which temperature is determined by the average transmit power, e.g., ⅛ W.

A natural way of increasing the bit rate in GSM is to allocate more than one time slot per user per frame, which concept is referred to above as "multi-slot" operation. When transmitting N out of 8 time slots per frame, the average consumed power is N/8 W. Thus, the power is increased proportionally to the bit rate, i.e. the range of transmission (cell size) is maintained. If the mobile were to transmit in all 8 time slots, the power consumption is 1 W.

As mentioned above, the modulation type may also be varied to adjust the transmission rate. For example, in today's GSM and GPRS standards, the selected modulation is GMSK which is a "constant envelope" type of modulation. This type of modulation can be implemented with a relatively high degree of efficiency, i.e., most of the power is transformed into an electromagnetic signal. In future enhancements of the physical layer of GPRS, referred to as EDGE, it is anticipated that the selected modulation will be 8PSK. 8PSK is a non-constant envelope type of modulation, which will reduce the efficiency of the power amplifier, i.e., increase the heat generated by mobile stations.

These trends in offering increased bit rate by allocating more time slots to a user and evolving to a more capacity efficient, but power hungry modulation method, will lead to increased problems with temperature problems. Although the foregoing examples are couched in terms of TDMA systems, CDMA systems face similar power issues wherein additional spreading codes can be allocated to provide greater througput and/or variable spreading factors can be employed wherein code puncturing is used to adjust the data transmission rate. In fact, Applicant expects that the difficulty in dissipating heat will be more likely to limit product offerings on the uplink than signal processing constraints.

As mentioned above, one relatively crude technique for managing temperature control of mobile stations is to simply provide a temperature measurement device in the mobile station and reduce the transmission rate when the temperature exceeds a threshold. According to one exemplary embodiment of the present invention, however, Applicant envisions additional cooperation between the mobile station and the system in handling this type of temperature-related transmission adjustment.

For example, in current GSM systems the mobile station is required to perform a signal strength measurement on another carrier (i.e., other than its currently assigned traffic channel carrier) once every TDMA frame. This process is referred to as performing Mobile Assisted Handoff (MAHO) measurements. In GPRS there is a similar measurement requirement, but in this case used for cell reselection. For a single frequency synthesizer, it takes some time to move the frequency to the intended channel, perform the measurement, and then return to the channel traffic frequency.

Given this constraint, a typical maximal number of time slots per frame that a mobile can receive and/or transmit in is five in GSM or GPRS systems, not all eight which are available in each TDMA frame. (However, Applicant has also envisioned the possibility that in future systems, mobile stations may be permitted to transmit and/or receive information using more timeslots to increase throughput, see U.S. Pat. No. 6,018,661, entitled "Inhibiting and Controlling Signal Strength Measurements by a Mobile Station in a Wireless Communication System", to Raith et al., the disclosure of which is incorporated here by reference). The GPRS specification allows for overhead signaling where the mobile indicates it capability to the system. There are several capability classes defined. The capability class can, for example, be expressed as maximum of the sum of transmit and receive slots, e.g., 5. The mobile station can, for example, enter into an operating mode where it receives in 4 slots and transmits in 1 slot or another operating mode wherein it receives in 3 slots and transmits in 2.

According to exemplary embodiments of the present invention, the mobile station can vary its resource usage to lower its transmit power when the mobile station determines that its operating temperature is too high, however the mobile station will send a message informing the base station of this change or, in the alternative, requesting the change. The message can be newly defined for this purpose, can be implemented as a new information element of an existing message, e.g., the aforedescribed capability report, or can be included by populating an existing information element (e.g., regarding TX capabilities) with the newly requested value/class mark or the already changed value/ class mark. A separate information element can be provided regarding whether this message is a request to change the transmission rate or informing the system of a previously implemented rate adjustment. This information is then used by the system to reallocate resources, e.g., air interface resources.

The transmission rate change handshaking between the mobile station and the base station could take many forms. For example, the mobile station could request the rate change and await a positive acknowledgement prior to implementing the change, the mobile station could request the rate change and await a negative acknowledgement for a predetermined time at which time it would undo the change, or the mobile station could simply implement the transmission rate change and inform the system accordingly.

Consider, for example, GPRS systems which allow for a mode where, until otherwise signaled, the mobile station is reserved particular timeslots in the uplink for transmission. Reservation mechanisms are employed, for example, to avoid situations wherein different mobile stations attempt to transmit data to the system on the same resource at the same time. Readers having an interest in more detail regarding reservation mechanisms used in radiocommunication systems are directed to U.S. patent application Ser. No. 08/796,110, entitled "Packet Control Channel Feedback Support for Contention and Reservation Based Access", filed Feb. 5, 1997, the disclosure of which is incorporated here by reference.

If, however, the mobile station simply begins to omit transmitting data on some of its reserved timeslots in the uplink due to heat problems, these time slots would be wasted since no other user is allowed to make an initial access or bit rate expansion using these slots. Therefore, according to the present invention, the mobile station informs the system that it needs to back-off from its current transmission rate, so that the system can reallocate resources, e.g.,make these timeslots available for other purposes. For example, a mobile station that is transmitting in triple rate (e.g., all three channels on a radio frequency in TIA/EIA 136 system referred to here as channels A, B and C) might transmit data bursts 1, 2, 3, 4, 5, 6 and 7 as:

Frame 1: A1, B2, C3 Frame 2: A4, B5, C6 Frame 3: A7, . . .

However, if the mobile station then drops back to double rate, its transmission pattern might be shown as:

Frame 1: A1, B2 Frame 2: A3, B4 Frame 3: A5, B6 . . .

Thus, channel C is available for usage by another mobile station and an indication of such can be sent to the system. By sending an explicit indication to the base station that the mobile has to back-off on its transmit resource usage, the same mobile station can benefit in that its downlink allocation can be increased and/or other users can benefit by obtaining additional transmit resources.

Figure 2:
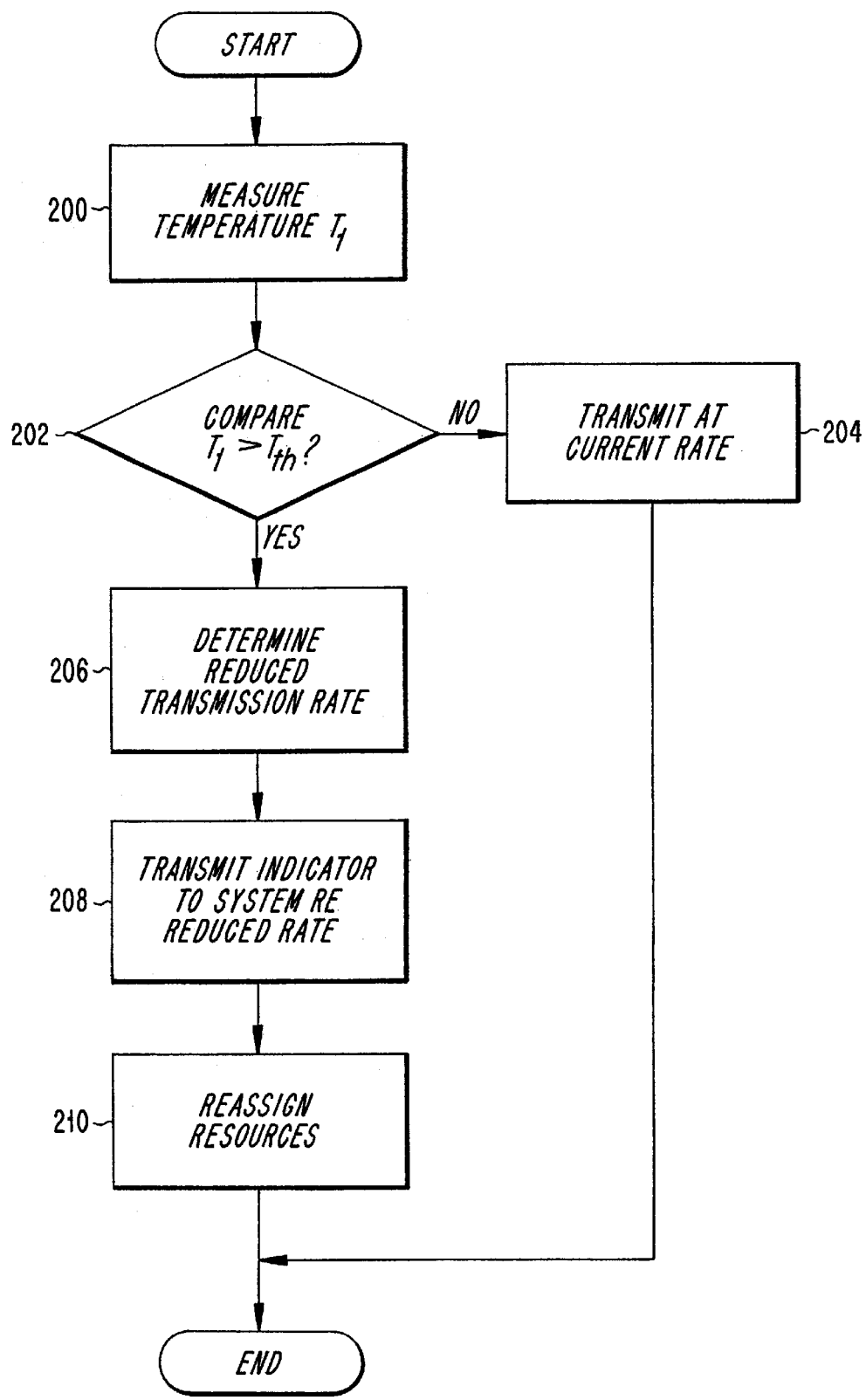
FIG. 2 is a flowchart depicting an exemplary embodiment of the present invention.

An illustration of an exemplary method in accordance with this exemplary embodiment is provided as FIG.2. Therein, at step 200, the temperature $T_1$ of the mobile station is measured using device or sensor 195. A comparison with a stored threshold temperature $T_{th}$ is performed at decision block 202. If the mobile station is not overheating, e.g., $T_1 < T_{th}$, then the flow moves to block 204 wherein the mobile station transmits at its currently assigned rate, using its currently assigned resources. Otherwise, if the mobile station is getting too hot, the flow proceeds to block 206 wherein a reduced rate is determined. For example, if a mobile station is transmitting using 4 timeslots, and $T_{th}$ is much greater than $T_1$, then the mobile station may reduce its transmission rate to using 1 timeslot. Thus, the amount of reduction in the transmission rate may also be related to the measured temperature.

In any event, once a new transmission rate is determined, the mobile station transmits an indicator to the system regarding the mobile station's new transmission rate at step 208. This permits the system to reallocate the resources previously assigned to the mobile station at step 210. Depending upon the type of system, this reallocation process may include, for example, assigning released uplink timeslots to other mobile stations, assigning released uplink spreading codes to other mobile stations, and/or assigning additional downlink timeslots to the mobile station which is reducing its transmission rate. Those readers interested in variable rate transmission systems in a TDMA environment are directed to U.S. Pat. No. 5,987,019, entitled "Multi-Rate Radiocommunication Systems and Terminals", to Raith et al. For an example of variable rate transmissions in CDMA environment, see U.S. Pat. No. 6,108,369, entitled "Channelization Code Allocation for Radio Communication Systems", to Ovesjö et al. The disclosures of these latter two patent applications are also expressly incorporated here by reference.

As an alternative, upon determining that the mobile station has exceeded a first temperature level (a warning level), the mobile station may request a reduction in its transmission rate or transmit power. Then, the mobile station can await an indication from the system that it may perform the requested reduction, or in the alternative, the absence of a negative response from the system. If the mobile station subsequently measures a temperature which exceeds a second level (a danger level) it may then autonomously reduce its transmission rate or transmit power.

According to other exemplary embodiments of the present invention, in addition to (or instead of) informing the system of a change in transmission rate, the mobile station 120 can inform the user of (1) warnings that the mobile station is heating up to a point where it may impact the transmission rate, and/or (2) an indication of an actual transmission rate change. For example, mobile station 120 can, upon measuring a temperature that is approaching $T_{th}$ provide an alert to the user, e.g., an iconic alert, a sound or voice alert. By informing the user of this heat condition, the user may be able to adjust his or her usage of the mobile station in such a way as to reduce its transmitted power and, therefore, the mobile station's temperature. For example, the user can attempt to improve the system's reception of the mobile station's transmissions by moving to a less obstructed site to reduce attenuation and take advantage of the system's power control mechanism (described below) or can move a small distance (or simply adjust the antenna) to attempt to reduce Rayleigh fading.

To provide the user with some feedback, another indicator may be displayed on mobile station 120 which informs the user of the mobile station's current operating parameters with respect to temperature reduction. For example, the mobile station can provide an indication of its current transmit power or a bar indicating some combination of its transmit power on the uplink and received signal strength on the downlink. This provides the user with more rapid feedback than an indicator of measured temperature, which measured temperature will only slowly decrease after the transmit power is reduced.

If user intervention is successful in avoiding a transmission rate change, i.e., if the measured temperature doesn't cross $T_{th}$, then no further action may be needed. If, on the other hand, a transmission change is needed, the mobile station can also inform the user of the new transmission rate via its display 190. This third type of indicator can be displayed along with the above-described heat indicator which will inform the user that the reduced transmission rate was the result of a high operating temperature. Moreover, the transmission rate indicator can be expressed as a percentage of a maximum transmission rate (e.g., of the mobile station or what is possible over the connection given the capabilities of the mobile station and base station), e.g., a bar showing 75% of maximum on the display. Alternatively, the transmission rate indicator can be expressed as a percent reduction from the maximum transmission rate. This indicator can be independent of the burstiness of the current application and the access multiplexing of the users on the channel, i.e., informing the user of the mobile station's current, heat-related capability rather than the instantaneous transmission rate of a given burst of data. Alternatively, or in addition thereto, an indicator could be provided which indicates instantaneous transmission and/or reception of data. Any other desired alarm/alert can also be generated by the mobile station to indicate a change in transmission rate, e.g., a tone, sound effect, voice alert, etc.

As mentioned above, many radiocommunication systems use a form of closed-loop power control to maintain a mobile station's transmit power at an optimal level to support high quality communications without undue interference. Generally speaking, closed loop power control refers to the capability of the system to monitor the quality and/or received signal strength of signals transmitted by mobile stations and send power control commands in accordance therewith. For example, if a base station 110 receives a packet from a mobile station 120 which has more than a predetermined number of bit errors, then the base station will return a transmit power control command in a subsequent packet on the downlink indicating that the mobile station should increase its transmit power. Conversely, if the base station receives a packet at a signal strength which is higher than necessary to accurately decode the information, it will return a power control command which instructs the mobile station to reduce its transmit power.

Thus, the user could move toward an open area, e.g., out of a building, nearer to a window, out of a car, etc. In this way, the system may decide to instruct the mobile station to reduce its transmit power, which will in turn reduce the heat dissipated by the power amplifier and permit the mobile station to return to its original transmission rate.

According to yet another exemplary embodiment of the present invention, the measured temperature of the mobile station and the status of current transmissions can be taken into account in determining when and how to adjust transmissions from the mobile station. For example, exemplary embodiments of the present invention provide for a determination of the mobile station's transmit position within higher layer messages, i.e., how much of a higher layer message has been transmitted, prior to determining whether to slow down or halt transmissions due to heat. This may reduce the impact of heat-related transmission adjustments, because recovery of transmitted information may be easier if complete higher layer messages are transmitted.

Figure 3:
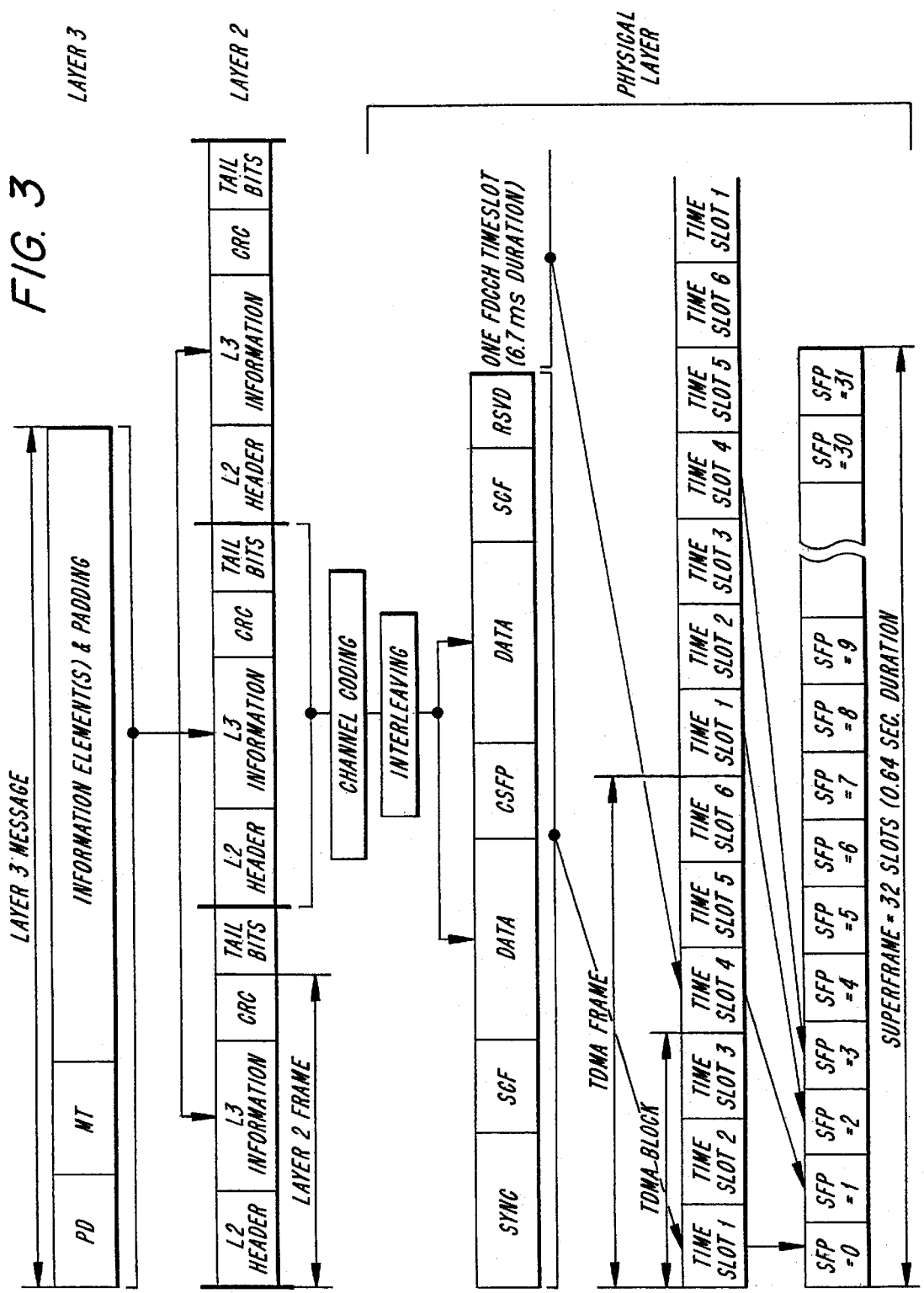
FIG. 3 is an exemplary mapping between layers in an exemplary TIA/EIA 136 compliant radiocommunication system.

To better understand the ramifications of higher/lower layer transmissions, consider the exemplary mapping illustrated in FIG. 3 for the digital control channel as described in TIA/EIA 136. Note, however, that use of this exemplary digital control channel mapping is purely illustrative and that the present invention finds particular applicability in other contexts, e.g., transmission of data packets on a packet data channel, which other contexts may use different terminology (e.g., LLC frames and MAC layer frames) to express relationships between layers. Rather than add the pages of description necessary for a complete understanding of each labelled field in FIG.3, the interested reader is referred to the standard specification TIA/EIA 136 (Parts 010-720), dated Feb. 6, 1998, which document is incorporated here by reference. Of interest for the present discussion is the mapping between the Layer 3 message into three Layer 2 messages (which include the Layer 3 information plus a header, cyclic redundancy check (CRC) and tail bits) into Layer 1 (physical layer) messages. It can be seen that each higher layer message is transmitted in a plurality of lower layer messages and, ultimately, in a number of TDMA bursts. According to this exemplary embodiment of the present invention, it is preferable to complete higher layer messages prior to terminating transmission or reducing transmission rates. This may avoid the need to retransmit data blocks and may reduce delay associated with completing the decoding of Layer 3 messages. Thus, for example, if the mobile station still needs to send one more TDMA burst to complete a particular Layer 3 message (or one more Layer 3 message to complete a higher layer message), the present invention may take that into account in determining the mobile station's transmission mode in addition to measured temperature.

Figure 4:
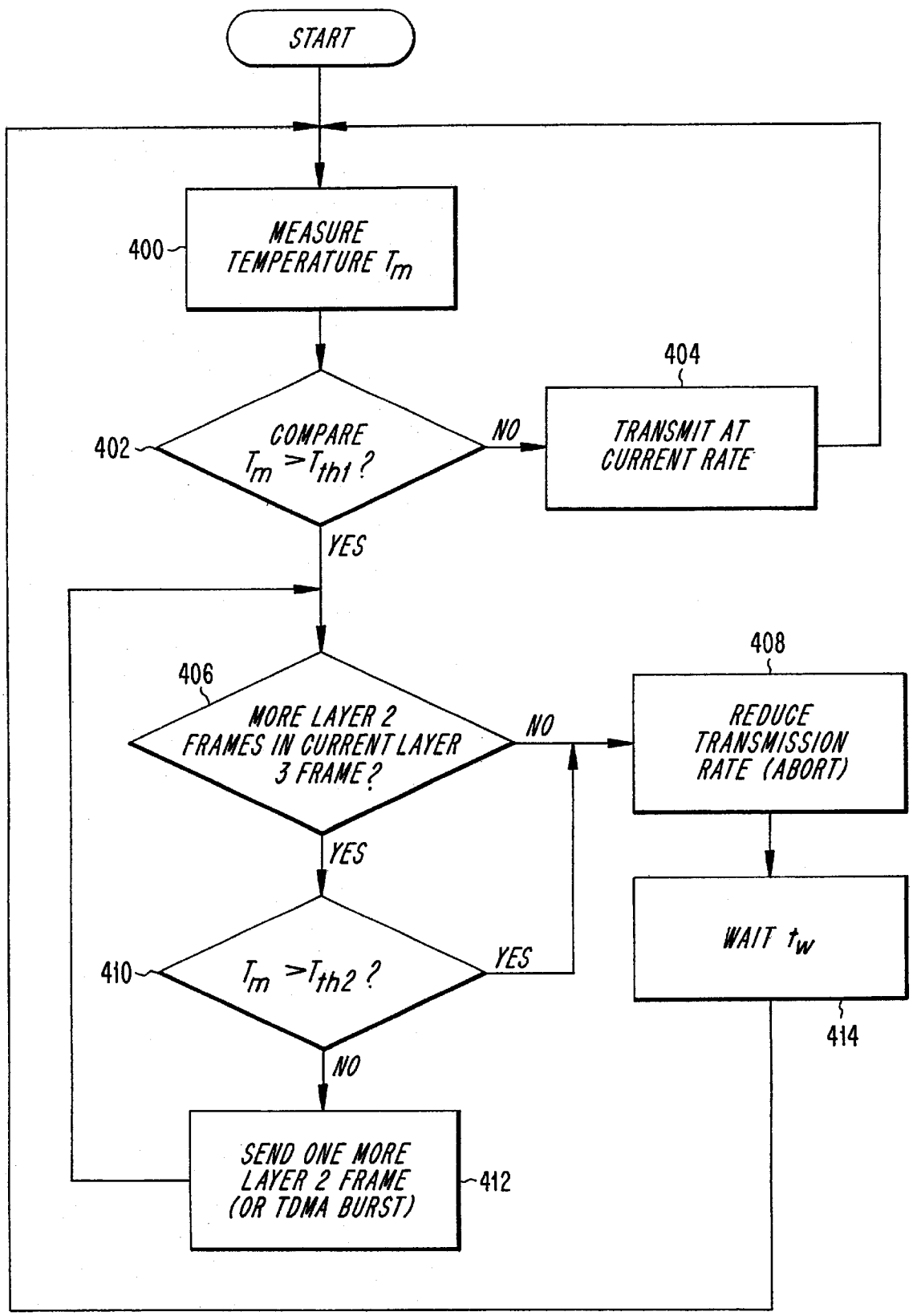
FIG. 4 is a flowchart depicting another exemplary embodiment of the present invention.

An exemplary method according to this exemplary embodiment will now be described with respect to FIG. 4. Therein, the current operating temperature of the mobile station is measured at block 400. At step 402, if the measured temperature $T_m$ is less than a first threshold $T_{th1}$, then the transmission can continue at a current transmission rate at step 404. Otherwise, the mobile station 120 determines whether it has completed its current higher layer frame, e.g., whether there are any TDMA bursts or Layer 2 frames remaining to be transmitted within a current Layer 3 message, at step 406. If not, the mobile station reduces its transmission rate or aborts transmission entirely due to heat at step 408.

If the mobile station is too hot, but has remaining lower layer frames to send to complete a higher layer frame, it may continue to try to send data packets. At step 410, the mobile station compares the measured temperature $T_m$ with a second threshold $T_{th2}$. If the temperature is greater than this second threshold, then the mobile station cannot complete the higher layer message and returns to step 408 where it takes appropriate action to reduce its transmit power. Otherwise, the mobile station transmits one more lower layer frame (e.g., a Layer 2 frame or TDMA burst) at step 410 and the flow circles back to determine whether the higher layer frame is completed.

Once the mobile station completes its higher layer frame or exceeds the second temperature threshold, it will reduce its transmission rate (or abort operations). However, it may be desirable to give the mobile station an opportunity to increase its transmission rate (or reestablish active transmission) after a cooling period. Thus, after some predetermined time period $t_w$, the flow can return to check the mobile station's temperature again at block 400. Of course those skilled in the art will appreciate that the exemplary embodiment illustrated in FIG. 4 can be combined with either of the foregoing exemplary embodiments, i.e., can include informing the system regarding reductions in transmission rates (as well as Layer 3 abortions and increases in the transmission rate after the cooling period) and can include informing the user of any or all of these decisions.

Although the foregoing has been described in the context of packet data, those skilled in the art will appreciate that the present invention can also be applied to circuit switched operation. There are two types of circuit switched operation—synchronous and asynchronous. Synchronous operation inherently requires a fixed bit rate and, therefore, a reduction in the transmission rate is not currently envisioned. However, the exemplary embodiment described below, wherein the transmit power is directly reduced, is readily applicable to synchronous operation.

For asynchronous operation, such as is found in systems operating in accordance with TIA/EIA IS-130 or the GSM based asynchronous data service, the present invention is more readily applicable. However, depending on the implementation in the base station, the system may be confused if there is no power, synchword, codes, etc., when it expects the presence of a signal. The data protocols in these types of systems contain frames which are numbered, thus the higher layer protocol may very well be able to handle situations wherein a mobile station is autonomously adjusting its transmit resources, e.g., from 2 time slots to 1 time slot. However, the management functionality of the base station may equate such an independent change in transmission with a major error event, thereby possibly disconnecting the call. Thus, in this asynchronous, circuit-switched context, explicit signaling by the mobile station informing (or possibly requesting) a fall-back to a lower bit rate (e.g., less time slot utilization) may also be useful.

Figure 5:
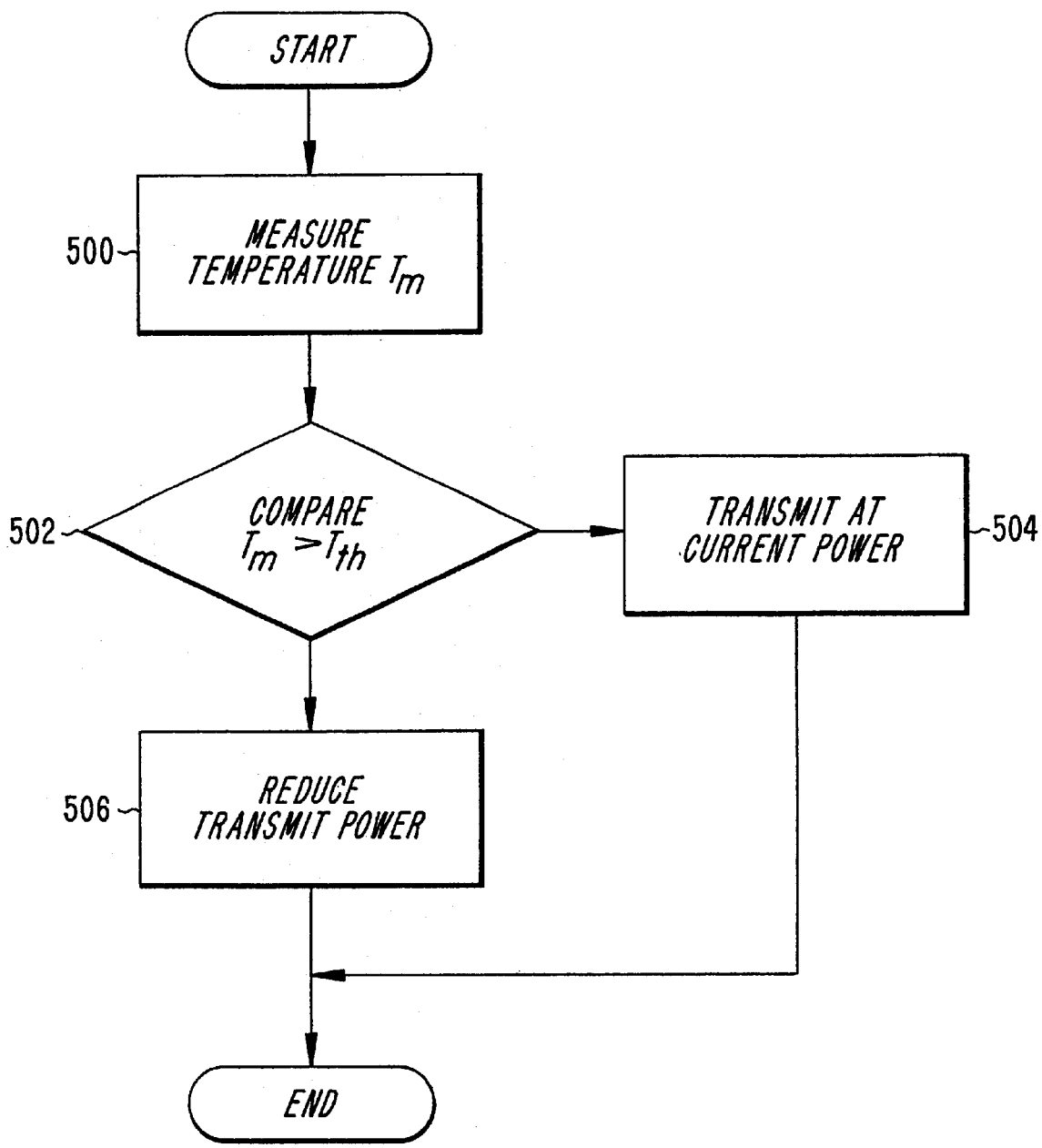
FIG. 5 is a flowchart depicting still another exemplary embodiment of the present invention.

According to yet another exemplary embodiment of the present invention, the mobile station can directly adjust its transmit power rather than indirectly adjusting transmit power by varying its transmission rate. A method according to this exemplary embodiment is depicted as FIG. 5. Therein, the temperature $T_m$ is measured at step 500. If the measured temperature is less than a threshold temperature (step 502), then the mobile station continues to transmit at a current power level. Otherwise, if, for example, the mobile station is beginning to overheat, the mobile station reduces its transmit power by 0.5 dB, at step 506. If the system determines that its received signal quality on the uplink is too low, e.g., due to the mobile station's transmit power reduction, then it can send a transmit power control command to the mobile station ordering the mobile to increase its transmit power. If this occurs, then the mobile station may then increase its transmit power and reduce its transmission rate in accordance with any of the foregoing exemplary embodiments, e.g., sending a message requesting (or informing) the system of the reduced transmission rate.

Figure 6:
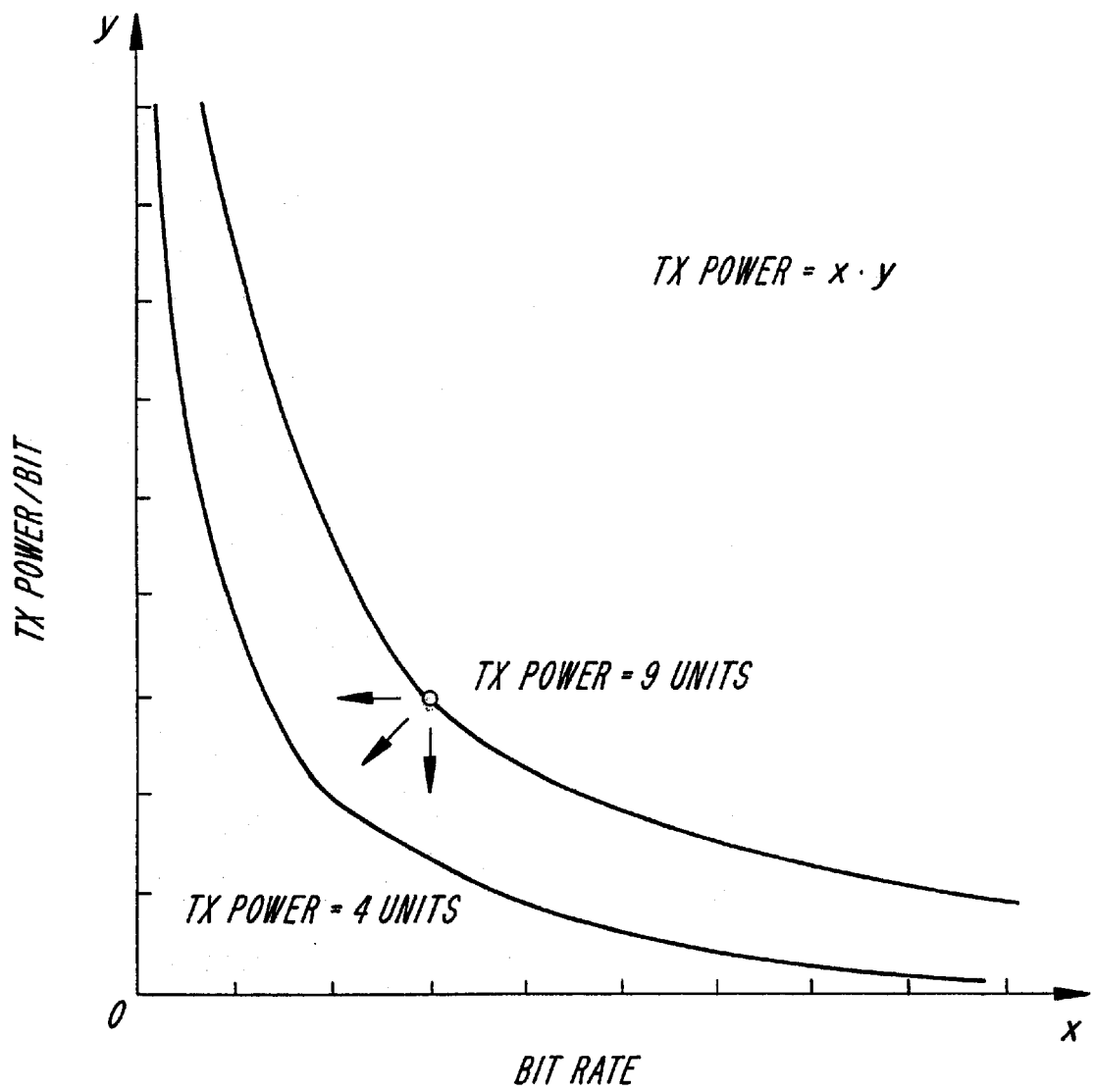
FIG. 6 is a graph illustrating exemplary relationships between transmit power per bit, bit rate and total transmit power.

As yet another alternative, when a temperature threshold is exceeded, the mobile station could perform both transmit power reduction and transmission rate reduction in order to reduce its operating temperature. That is, for example, the mobile station could transmit in fewer timeslots and with lower power to reduce its total transmit power. Consider FIG. 6, wherein exemplary relationships between the transmit power per bit, bit rate and total transmit power are illustrated. Therein, it can be seen that to reduce the total transmit power from nine units to four units, various approaches could be adopted to move from the TX Power=9 curve to the TX Power=4 curve. The mobile station could just reduce its bit rate, could just reduce its transmit power per bit or could reduce some combination of bit rate and power per bit.

Although the invention has been described and illustrated with reference to specific embodiments thereof, it is not intended that the invention be limited to these illustrative embodiments. Those skilled in the art will recognize that modifications and variations can be made without departing from the spirit of the invention.

What is claimed is:

1. A method for controlling a temperature level of a mobile station in a radiocommunication system, said method comprising:
   measuring a temperature associated with said mobile station;
   adjusting an operating parameter associated with said mobile station responsive to said measured temperature; and
   providing an indication at said mobile station to alert a user of said mobile station that said operating parameter has been adjusted responsive to said temperature.

2. The method of claim 1, wherein adjusting an operating parameter associated with said mobile station responsive to said measured temperature further comprises:
   requesting an adjustment of said operating parameter from said radiocommunication system; and
   adjusting said operating parameter responsive to an indication provided by said radiocommunication system granting said request.

3. The method of claim 2 further comprising notifying said radiocommunication system that said operating parameter has been adjusted.

4. The method of claim 2, wherein requesting the adjustment of said operating parameter from said radiocommunication system further comprises providing said temperature to said radiocommunication system.

5. The method of claim 1, wherein adjusting said operating parameter responsive to an indication provided by said radiocommunication system granting said request comprises:
   comparing said temperature with a first threshold; and
   adjusting said operating parameter responsive to said temperature if said temperature exceeds said first threshold.

6. The method of claim 5, wherein adjusting said operating parameter responsive to said temperature if said temperature exceeds said first threshold further comprises:
   comparing said temperature with a second threshold, greater than said first threshold; and
   adjusting said operating parameter if said measured temperature exceeds said second threshold without performing said request.

7. The method of claim 6, further comprising storing said first threshold and said second threshold in a memory.

8. The method of claim 7, wherein storing said first threshold and said second threshold in a memory further comprises storing said first and second thresholds and one or more capabilities of said mobile station at a predetermined address.

9. The method of claim 8, wherein said one or more capabilities are determined by a user subscription.

10. The method of claim 9, wherein one or more limitations of said user subscription are stored on a subscriber interface module (SIM).

11. The method of claim 1, wherein said indication further comprises a visual indication on a display associated with said mobile station.

12. The method of claim 11, wherein said visual indication further comprises an icon provided on said display.

13. The method of claim 12, wherein said visual indication is proportional to said temperature.

14. The method of claim 13, wherein said visual indication is proportional to said operating parameter.

15. The method of claim 1, wherein said indication further comprises an audible indication provided on an audio output associated with said mobile station.

16. The method of claim 15, wherein said audible indication further comprises a voice indication provided on said audio output.

17. The method of claim 1, wherein adjusting an operating parameter associated with said mobile station responsive to said measured temperature further comprises restoring said operating parameter to a pre-adjustment level after a time interval expires.

18. The method of claim 17, wherein adjusting an operating parameter associated with said mobile station responsive to said measured temperature further comprises restoring said operating parameter to a pre-adjustment level when said temperature reaches a predetermined level.

19. The method of claim 1, wherein said operating parameter comprises transmit power.

20. The method of claim 1, wherein said operating parameter comprises a data transmission rate.

21. The method of claim 1, wherein said operating parameter comprises modulation type.

22. The method of claim 21, wherein said modulation comprises a constant envelope modulation type.

23. The method of claim 22, wherein said constant envelope modulation type comprises Gaussian Minimum Shift Keying (GMSK) modulation.

24. The method of claim 21, wherein said modulation type comprises a non-constant envelope modulation type.

25. The method of claim 24, wherein said non-constant envelope modulation types comprises 8 Phase Shift Key (8PSK) modulation.

26. The method of claim 1, wherein said mobile station is a PCMCIA module connected to a general purpose computer.

27. The method of claim 1, further comprising transmitting an indication from said mobile station to said system of said measured temperature level, and further comprising transmitting a request to establish a reduced transmission rate.

28. A mobile station comprising:
a processor, said processor configured to:
measure a temperature associated with said mobile station;
adjust an operating parameter associated with said mobile station responsive to said temperature; and
provide an indication at said mobile station to alert a user of said mobile station that said operating parameter has been adjusted responsive to said temperature.

29. The mobile station of claim 28, wherein said mobile station is configured to:
request an adjustment of said operating parameter from a base station; and
adjust said operating parameter responsive to an indication provided by said base station.

30. The mobile station of claim 29, wherein said mobile station is further configured to notify said base station that said operating parameter has been adjusted.

31. The mobile station of claim 30, wherein said processor is further configured to restore said operating parameter to a pre-adjustment level after a time interval expires.

32. The mobile station of claim 31, wherein said processor is further configured to restore said operating parameter to a pre-adjustment level when said measured temperature reaches a predetermined level.

33. The mobile station of claim 29, wherein said mobile station is further configured to provide said measured temperature to said base station.

34. The mobile station of claim 29, wherein said processor is further configured to:
compare said measured temperature with a first threshold; and
adjust said operating parameter responsive to said measured temperature if said measured temperature exceeds said first threshold.

35. The mobile station of claim 34, wherein said operating parameter is a transmit power level, and wherein mobile station is further configured to reduce said transmit power level by predetermined increments.

36. The mobile station of claim 29, wherein said processor is further configured to:
compare said measured temperature with a second threshold, greater than said first threshold; and
adjust said operating parameter if said measured temperature exceeds said second threshold without performing said request.

37. The mobile station of claim 36, wherein said mobile station further comprises a memory, and wherein said processor is further configured to store said first threshold and said second threshold in said memory.

38. The mobile station of claim 37, wherein said mobile station is further configured to store said first and second thresholds and one or more capabilities of said processor at a predetermined address.

39. The mobile station of claim 38, wherein said one or more capabilities are determined by a user subscription.

40. The mobile station of claim 39, wherein one or more limitations of said user subscription are stored on a subscriber interface module (SIM).

41. The mobile station of claim 40, wherein said mobile station is further configured to receive said one or more limitations of said user subscription at call setup.

42. The mobile station of claim 41, wherein said mobile station receives an initial transmission rate from a base station.

43. The mobile station of claim 42, wherein said mobile station receives one or more capabilities of said mobile station from said base station.

44. The mobile station of claim 43, wherein said one or more capabilities of said mobile station are retrieved from a mobile station home location register (HLR).

45. The mobile station of claim 28, further comprising an output device, said output device comprising a display and wherein said indication further comprises a visual indication on said display.

46. The mobile station of claim 45, wherein said visual indication further comprises an icon.

47. The mobile station of claim 46, wherein said visual indication is proportional to said measured temperature.

48. The mobile station of claim 47, wherein said visual indication is proportional to said operating parameter.

49. The mobile station of claim 28, further comprising an output device, said output device comprising a speaker, and wherein said indication further comprises an audible indication provided on said speaker.

50. The mobile station of claim 49, wherein said audible indication further comprises a voice indication.

51. The mobile station of claim 28, wherein said operating parameter comprises a transmit power level.

52. The mobile station of claim 28, wherein said operating parameter comprises a data transmission rate.

53. The mobile station of claim 28, wherein said operating parameter comprises a modulation type.

54. The mobile station of claim 53, wherein said modulation type comprises a constant envelope modulation type.

55. The mobile station of claim 54, wherein said constant envelope modulation type comprises Gaussian Minimum Shift Keying (GMSK) modulation.

56. The mobile station of claim 53, wherein said modulation type comprises a non-constant envelope modulation type.

57. The mobile station of claim 56, wherein said non-constant envelope modulation type comprises 8 Phase Shift Key (8PSK) modulation.

58. The mobile station of claim 28, wherein said mobile station is a PCMCIA module connected to a general purpose computer.

59. The mobile station of claim 28, wherein said mobile station receives an indication of one or more capabilities of a base station on a broadcast control channel.

60. The mobile station of claim 59, wherein said one or more capabilities further comprises adjustment capabilities for adjusting said operating parameter.

61. The mobile station of claim 60, wherein said processor is further configured to analyze said adjustment capabilities of said base station to determine the maximum achievable transmission rate associated with said base station.

62. The mobile station of claim 28, wherein said indication is provided prior to adjusting said operating parameter.

63. A method for controlling a temperature level of a mobile station, said method comprising:

measuring a temperature associated with said mobile station;

determining a current transmission status of said mobile station; and adjusting a data transmission rate associated with said mobile station responsive to said measured temperature and said current transmission status of said mobile station.

64. The method of claim 63 further comprising:

transmitting an indication to said radiocommunication system indicating said adjustment of said transmission rate.

65. The method of claim 63, further comprising:

providing an indication that said transmission rate is adjusted.

66. The method of claim 65, further comprising:

providing an indication at that said adjustment is heat related.

67. The method of claim 63 further comprising comparing said measured temperature to a first threshold and wherein adjusting a data transmission rate associated with said mobile station responsive to said measured temperature and said current transmission status of said mobile station comprises adjusting said data transmission rate if said measured temperature exceeds said first threshold.

68. The method of claim 67 further comprising comparing said measured temperature to a second threshold, and wherein adjusting said data transmission rate if said measured temperature exceeds said first threshold comprises immediately reducing said data transmission rate if said measured temperature exceeds said second threshold.

69. The method of claim 68 wherein adjusting said data transmission rate if said measured temperature exceeds said first threshold further comprises reducing said data transmission rate after completion of said transmission if said measured temperature exceeds said first threshold and is less than said second threshold.

70. The method of claim 63 wherein determining a current transmission status of said mobile station comprises determining how much of a message has been transmitted from said mobile station.

71. A mobile station comprising:

a processor configured to:

measure a temperature associated with said mobile station;

determine a current transmission status of said mobile station; and adjust a data transmission rate associated with said mobile station responsive to said measured temperature and said current transmission status of said mobile station.

72. The mobile station of claim 71 wherein said processor is further configured to compare said measured temperature to a first threshold and adjust said data transmission rate if said measured temperature exceeds said first threshold.

73. The mobile station of claim 72 wherein said processor is further configured to compare said measured temperature to a second threshold and immediately reduce said data transmission rate if said measured temperature exceeds said second threshold.

74. The mobile station of claim 73 wherein said processor is configured to reduce said data transmission rate after completion of said transmission if said measured temperature exceeds said first threshold and is less than said second threshold.

75. The mobile station of claim 71 wherein said processor is configured to determine a current transmission status of said mobile station and to determine how much of a message has been transmitted from said processor.

76. A mobile station comprising:

means for measuring a temperature level in said mobile station;

means for reducing a transmission rate associated with information transmission from the mobile station responsive to said measured temperature level; and means for providing an indication at said mobile station of said reduced transmission rate.

77. The mobile station of claim 76, wherein said means for providing an indication comprises a display attached to said mobile station.

* * * * *